United States Patent
Wang et al.

(10) Patent No.: US 9,629,748 B2
(45) Date of Patent: Apr. 25, 2017

(54) MULTI-STAGE TUBING FOR HIGH-SPEED PNEUMATIC SURGICAL CUTTER

(75) Inventors: Andrew Chen Wang, Fremont, CA (US); Daniel David Rogers, Oakland, CA (US)

(73) Assignee: Medical Instrument Development Laboratories, Inc., San Leandro, CA (US)

( * ) Notice: Subject to any disclaimer, the term of this patent is extended or adjusted under 35 U.S.C. 154(b) by 187 days.

(21) Appl. No.: 13/485,324

(22) Filed: May 31, 2012

(65) Prior Publication Data

US 2013/0325044 A1 Dec. 5, 2013

(51) Int. Cl.
*A61F 9/007* (2006.01)
*A61B 17/00* (2006.01)

(52) U.S. Cl.
CPC *A61F 9/00763* (2013.01); *A61B 2017/00544* (2013.01)

(58) Field of Classification Search
CPC ...... A61F 9/007; A61F 9/00763; A61B 17/32; A61B 2017/00544; A61B 2017/320028; F16L 11/00; F16L 11/121; Y10T 137/3724
USPC ....... 606/166, 169, 170, 171, 177, 178, 179, 606/180; 138/120, 125, 126; 30/392, 30/393, 394; 83/53, 177
See application file for complete search history.

(56) References Cited

U.S. PATENT DOCUMENTS

| | | | |
|---|---|---|---|
| 3,740,612 A | | 6/1973 | Gauthier et al. |
| 3,815,604 A | * | 6/1974 | O'Malley et al. ............. 604/22 |
| 3,994,297 A | | 11/1976 | Kopf |
| 4,009,912 A | * | 3/1977 | Mraz .............................. 406/144 |
| 4,418,596 A | * | 12/1983 | Garrocho .......................... 83/98 |
| 4,425,919 A | | 1/1984 | Alston, Jr. et al. |
| 4,456,000 A | * | 6/1984 | Schjeldahl et al. .......... 604/4.01 |
| 4,534,250 A | * | 8/1985 | Garrocho .......................... 83/98 |

(Continued)

FOREIGN PATENT DOCUMENTS

| | | | | |
|---|---|---|---|---|
| WO | 01/30281 | | 5/2001 | |
| WO | WO 0130281 A1 | * | 5/2001 | ............. A61F 9/007 |
| WO | WO0130281 A1 | * | 5/2001 | ............. A61F 9/007 |

OTHER PUBLICATIONS

International Search Report and Written Opinion for Application No. PCT/US2012/040210 dated Nov. 29, 2012 (15 pages).

*Primary Examiner* — Ryan J Severson
*Assistant Examiner* — Christian Knauss
(74) *Attorney, Agent, or Firm* — Michael Best & Friedrich LLP (57) ABSTRACT

Multi-stage tubing connecting a pneumatic pulse generator to a surgical cutter and for transmitting pressure pulses from the pneumatic pulse generator to the surgical cutter. The multi-stage tubing includes a first-stage and a second-stage. The first-stage has a first end connected to an output port of the pneumatic pulse generator, a second end opposite the first end, and a first inner channel for transmitting the pressure pulses to the surgical cutter. The first inner channel has a first cross-sectional area. The second-stage has a first end in pneumatic communication with the second end of the first-stage, a second end opposite the first end of the second-stage, and a second inner channel for transmitting the pressure pulses to the surgical cutter. The second inner channel has a second cross-sectional area that is different than the first cross-sectional area.

47 Claims, 9 Drawing Sheets

(56) References Cited

U.S. PATENT DOCUMENTS

| | | | | |
|---|---|---|---|---|
| 4,629,218 | A | 12/1986 | Dubois | |
| 5,226,910 | A * | 7/1993 | Kajiyama et al. | 606/171 |
| 5,314,440 | A * | 5/1994 | Shapiro | 359/676 |
| 5,421,230 | A * | 6/1995 | Flaherty et al. | 83/13 |
| 5,470,322 | A * | 11/1995 | Horzewski et al. | 604/524 |
| 5,487,725 | A | 1/1996 | Peyman | |
| 5,520,668 | A * | 5/1996 | Greff | A61M 1/008 604/319 |
| 5,549,547 | A * | 8/1996 | Cohen et al. | 604/30 |
| 5,562,691 | A * | 10/1996 | Tano et al. | 606/166 |
| 5,649,954 | A * | 7/1997 | McEwen | 606/202 |
| 5,788,667 | A | 8/1998 | Stoller | |
| 5,976,453 | A * | 11/1999 | Nilsson et al. | 264/555 |
| 5,997,562 | A * | 12/1999 | Zadno-Azizi et al. | 606/194 |
| 6,116,284 | A * | 9/2000 | Murray et al. | 138/39 |
| 6,277,096 | B1 | 8/2001 | Cortella et al. | |
| 6,336,471 | B1 * | 1/2002 | Feuling | 138/39 |
| 6,506,176 | B1 | 1/2003 | Mittelstein et al. | |
| 6,575,990 | B1 * | 6/2003 | Wang et al. | 606/171 |
| 6,579,484 | B1 * | 6/2003 | Tiernan et al. | 264/173.16 |
| 6,763,753 | B1 * | 7/2004 | Brumley et al. | 83/639.1 |
| 6,824,553 | B1 * | 11/2004 | Samson et al. | 606/192 |
| 7,422,035 | B2 | 9/2008 | Wu | |
| 7,443,296 | B2 * | 10/2008 | Mezhinsky et al. | 340/572.1 |
| 7,802,574 | B2 * | 9/2010 | Schultz | 128/207.14 |
| 8,070,712 | B2 | 12/2011 | Muri et al. | |
| 8,529,468 | B2 * | 9/2013 | Hoffa et al. | 600/567 |
| 2005/0085838 | A1 * | 4/2005 | Thompson et al. | 606/170 |
| 2005/0115624 | A1 * | 6/2005 | Walak | 138/139 |
| 2006/0224181 | A1 * | 10/2006 | McEwen et al. | 606/202 |
| 2006/0287672 | A1 * | 12/2006 | McEwen et al. | 606/202 |
| 2008/0023209 | A1 * | 1/2008 | Wang | 173/169 |
| 2009/0036878 | A1 * | 2/2009 | Vijfvinkel et al. | 606/4 |
| 2010/0305596 | A1 * | 12/2010 | Peterson et al. | 606/171 |
| 2011/0127767 | A1 * | 6/2011 | Wicks et al. | 285/319 |
| 2011/0144675 | A1 | 6/2011 | Gao et al. | |
| 2011/0204622 | A1 * | 8/2011 | Lewis et al. | 285/313 |
| 2013/0325044 | A1 * | 12/2013 | Wang et al. | 606/161 |

\* cited by examiner

MULTI-STAGE TUBING FOR HIGH-SPEED PNEUMATIC SURGICAL CUTTER

FIELD

Embodiments of the invention relate to surgical cutting devices and tubing used to transmit pressure pulses to such devices.

BACKGROUND

Surgical cutting devices are sometimes pneumatically driven. An ophthalmic cutting device is an example of such a surgical instrument and is used in eye surgery. A guillotine-style ophthalmic cutting device may be used to remove portions of the vitreous humor of the eye. A guillotine-style ophthalmic cutting device includes two principal parts: (1) a hollow needle including a cutting port and (2) a slidable (usually reciprocating), cutter positioned inside the needle. The cutter may also be hollow. In use, the ophthalmic cutting device is inserted into an incision in the eye. As vitreous tissue enters the port of the needle, the cutter slides past the port to cut the tissue. A vacuum may be applied to the cutter to remove the cut tissue from the cutting device.

SUMMARY

To move the cutter and perform the cutting, a driver, such as a pneumatic pulse generator, generates pressure pulses (e.g., of air or nitrogen) that are transmitted from the pressure pulse generator to the cutter via tubing connecting the cutting device to the driver. The cutter may be biased into a non-cutting position by a static biasing force (e.g., using a preloaded spring). The pressure pulses travel the length of the tubing and push the cutter against the bias (e.g., through a flexible diaphragm) and into a cutting position where the cutter slides past the cutting port of the needle and cuts the tissue. Between peaks of the pressure pulses, the pressure in the tubing is vented to atmosphere. Therefore, the pressure pulses return through the tubing to the pneumatic pulse generator, which allows the biasing force to return the cutter to the non-cutting position. Accordingly, each pressure pulse results in a cutting motion of the cutter.

In another embodiment, the cutter in the cutting device may have little or no biasing force holding the cutter in the non-cutting position. In this embodiment, two pneumatic pulses (for example, generated by two pulse generators) are used. A first pressure pulse generator transmits pressure pulses to the cutting device to force the cutter into the cutting position. A second pressure pulse generator transmits pressure pulses to restore the cutter to the non-cutting position. Therefore, this embodiment uses two parallel lengths of tubing to drive the cutting device. In some embodiments, the two pressure pulse generators are embodied as a single device. The single device can include two pulse generators, each with a separate output. In other embodiments, the device can include a single pulse generator and at least two outputs supplying pulse trains from the single pulse generator at different phases. The pulse trains may have different amplitudes, frequencies, and/or phases.

To provide precise cutting movements of the cutter, embodiments of the invention provide an ophthalmic surgical cutting apparatus. The surgical cutting apparatus includes a surgical cutter and a tubing assembly. The tubing assembly includes multi-stage tubing configured to be connected to a pneumatic pulse generator and to the surgical cutter. The multi-stage tubing transmits pressure pulses to the surgical cutter. The multi-stage tubing has a length of about two feet or more and includes a first-stage and a second-stage. The first-stage has a first end configured to be connected to an output port of the pneumatic pulse generator, a second end opposite the first end, and a first inner channel for transmitting the pressure pulses to the surgical cutter. The first inner channel has a first cross-sectional area. The second-stage has a first end configured to be in pneumatic communication with the second end of the first-stage, a second end opposite the first end of the second-stage, and a second inner channel for transmitting the pressure pulses to the surgical cutter. The second inner channel has a second cross-sectional area that is different than the first cross-sectional area.

Another embodiment of the invention provides an ophthalmic surgical cutting apparatus that includes a surgical cutter, a first tubing, and a second tubing. The first tubing is configured to transmit a first plurality of pressure pulses to the surgical cutter. The second tubing is configured to transmit a second plurality of pressure pulses to the surgical cutter. The first tubing includes multiple stages and has a length of about two feet or more. The multiple stages include a first-stage and a second stage. The first-stage has a first end configured to be connected to an output port of a pneumatic pulse generator, a second end opposite the first end, and a first inner channel for transmitting the first plurality of pressure pulses to the surgical cutter. The first inner channel has a first cross-sectional area. The second-stage has a first end configured to be in pneumatic communication with the second end of the first-stage, a second end opposite the first end of the second-stage, and a second inner channel for transmitting the first plurality of pressure pulses to the surgical cutter. The second inner channel has a second cross-sectional area that is different than the first cross-sectional area.

Further embodiments of the invention provide a tubing assembly including multi-stage tubing. The multi-stage tubing is configured to be connected to a pneumatic pulse generator and to a surgical cutter and transmits pressure pulses to the surgical cutter. The multi-stage tubing includes a first-stage and a second-stage. The first-stage has a first end configured to be connected to an output port of the pneumatic pulse generator, a second end opposite the first end, and a first inner channel for transmitting the pressure pulses to the surgical cutter. The first inner channel has a first cross-sectional area. The second-stage has a first end configured to be in pneumatic communication with the second end of the first-stage, a second end opposite the first end of the second-stage, and a second inner channel for transmitting the pressure pulses to the surgical cutter. The second inner channel has a second cross-sectional area that is different than the first cross-sectional area.

Yet further embodiments of the invention provide an ophthalmic surgical cutting apparatus having a surgical cutter and a tubing assembly. The surgical cutter is configured to be driven by a pneumatic pulse generator having an output port providing pressure pulses at a frequency of about 40 Hz or more. The tubing assembly includes multi-stage tubing connecting the pneumatic pulse generator to the surgical cutter and transmitting the pressure pulses from the pneumatic pulse generator to the surgical cutter. The multi-stage tubing has a length of about two feet or more and includes a first-stage tube and a second-stage tube. The first-stage tube has a first end configured to be connected to the output port of the pneumatic pulse generator, a second end opposite the first end, and a first inner channel for transmitting the pressure pulses to the surgical cutter. The first inner channel has a first diameter. The second-stage tube has a first end configured to be in pneumatic communication with the second end of the first-stage tube, a second end opposite the first end of the second-stage tube, and a second inner channel for transmitting the pressure pulses to the surgical cutter. The second inner channel has a second diameter that is different than the first diameter.

These and other aspects of the invention, together with the organization and operation thereof, will become apparent from the following detailed description when taken in conjunction with the accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
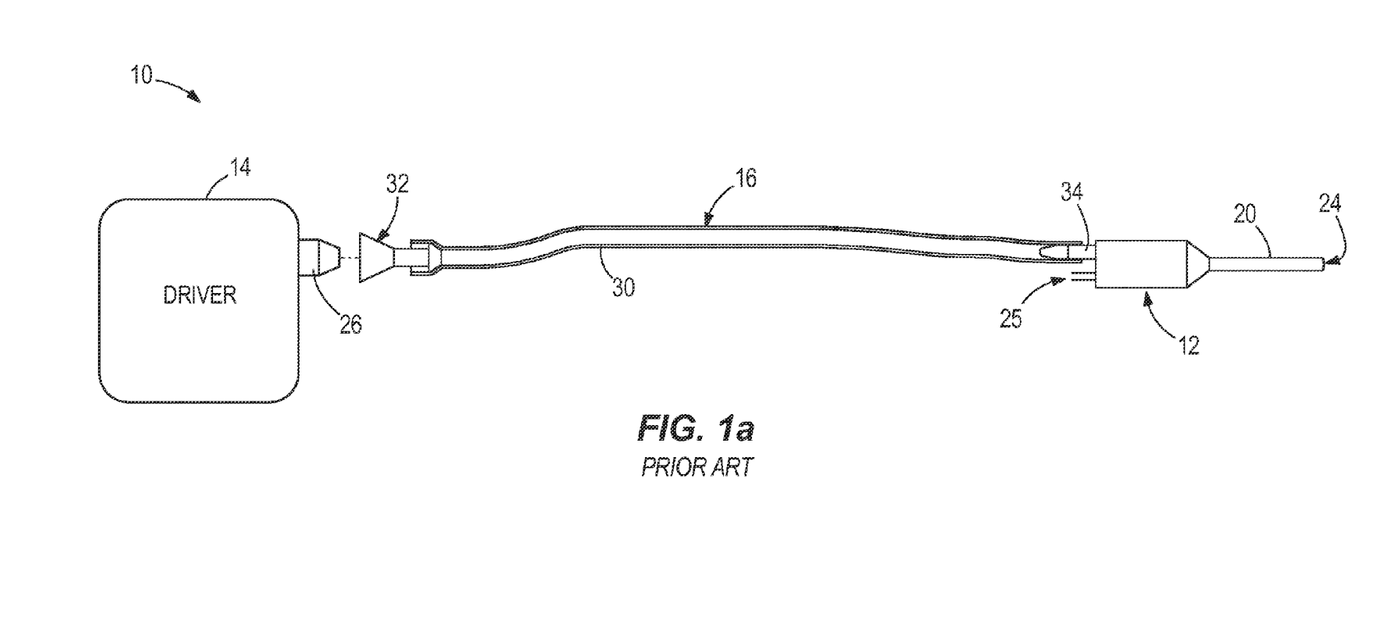
FIGS. 1a and 1b schematically illustrate prior art ophthalmic surgical cutting apparatuses in an exploded view.

FIG. 1a schematically illustrates a prior art ophthalmic surgical cutting apparatus 10. The apparatus 10 includes a surgical cutter 12, a pneumatic pulse generator or driver 14, and a tubing assembly 16. The surgical cutter 12 is used to perform eye surgeries and includes a hollow needle 20 and a cutter positioned inside the needle 20 (not shown). The cutter is slidable (e.g., reciprocating, vibrating, or a combination thereof) and has a stroke of about one millimeter. In use, surgical cutter 12 is inserted into an incision in the eye. As vitreous tissue enters a port 24 of the needle 20, the cutter moves past the port 24 to cut the tissue. In some embodiments, a vacuum is applied to an aspiration line 25 of the surgical cutter 12 to remove the cut tissue from the surgical cutter 12.

The driver 14 includes an output port 26. The driver 14 is configured to generate pressure pulses (e.g., of air or nitrogen) at a fixed or variable frequency. In some embodiments, a surgeon or other individual operating the driver 14 can select a desired frequency. For example, a surgeon can control the driver 14 to generate pressure pulses at a frequency from about 4 Hz to about 20 Hz to perform fast tissue removal or to generate a single pressure pulse for performing a single cut. A surgeon can also control the driver 14 to generate pressure pulses at a frequency from about 20 Hz to about 83 Hz to perform very small smooth cuts (e.g., near the retina). Therefore, the driver 14 can provide pressure pulses at a frequency from about 2 Hz to about 83 Hz. In some arrangements the driver 14 is part of a console, such as AVE ("Adjustable Vit Enhancer") console available from Medical Instrument Development Laboratories, Inc., which provides pressure pulses (i.e., pulse trains) at a frequency from about 10 Hz to about 42 Hz.

The driver 14 provides the generated pressure pulses to the output port 26. To generate the pressure pulses, the driver 14 includes a compressed gas or fluid source, such as air or nitrogen, and one or more solenoid valves, one or more motor-driven valves, a piston-type pressure pulse generator, or a combination thereof. In some embodiments, the driver 14 also includes one or more pressure regulators, one or more accumulators (e.g., capacitors), or a combination thereof to generate the pressure pulses in a predetermined waveform.

The tubing assembly 16 connects the surgical cutter 12 to the driver 14. The tubing assembly 16 includes a single piece of continuous tubing 30 having a length of about 80 inches (e.g., 78.7 inches). The tubing 30 includes a single channel having a constant inner diameter. The inner diameter of the tubing 30 is about $\frac{1}{16}$ of an inch. The tubing assembly 16 also includes a fitting 32 that allows the tubing 30 to be quickly connected to the output port 26 of the driver. In some arrangements, the fitting 32 is an oversized tube barb that holds the tubing 30 securing to the output port 26. At the other end of the tubing 16, the tubing fits over a connector 34 coupled to the surgical cutter 12.

The pressure pulses generated by the driver 14 travel the length of the tubing assembly 16 and force the cutter (e.g., through a flexible diaphragm) against a bias of the cutter (e.g., generated by a static biasing force, such as a preloaded spring) and into a cutting position where the cutter slides past the cutting port 24 of the needle 20 and cuts the tissue. Between peaks of the pressure pulses, the pressure in the tubing assembly 16 is vented to atmosphere. Therefore, the pressure pulses return through the tubing assembly 16 to the driver 14, which allows the biasing force to return the cutter to the non-cutting position. Accordingly, each pressure pulse results in a single cutting motion of the cutter.

Figure 1B:
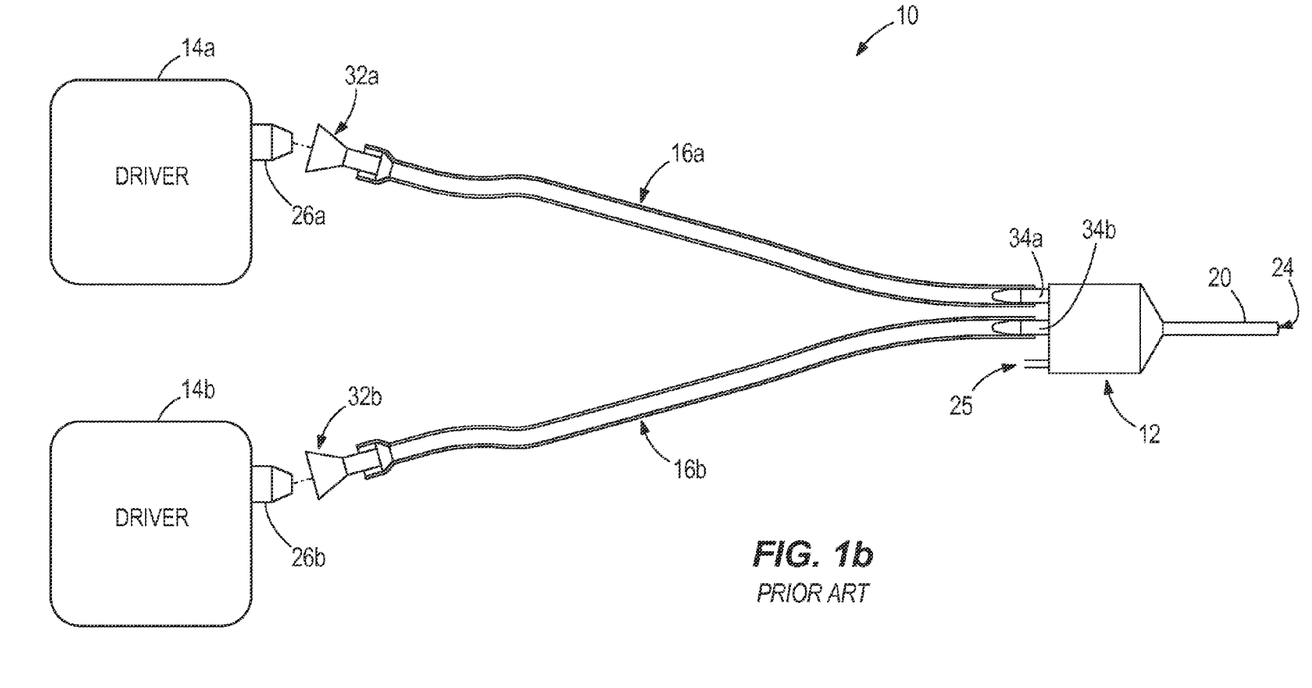

As noted above, in some embodiments, the cutter in the surgical cutter 12 may have little or no biasing force holding the cutter in the non-cutting position. In this embodiment, two pneumatic pulse generators or drivers and two tubing assemblies are used as illustrated in FIG. 1b. A first driver 14a transmits pressure pulses to the cutter via a first tubing assembly 16a to force the cutter into the cutting position. A second driver 14b transmits pressure pulses to the cutter via a second tubing assembly to restore the cutter to the non-cutting position. In some embodiments, the two drivers 14a and 14b are embodied as a single device. The single device can include two pulse generators, each with a separate output. In other embodiments, the single device can include a single pulse generator that supplies pressure pulses over two different outputs at different amplitudes, frequencies, and/or phases.

As illustrated in FIG. 1b, the tubing assemblies 16a and 16b have similar properties as the tubing assembly 16 described above with respect to FIG. 1a. In particular, each tubing assembly 16a and 16b includes the tubing 30 that includes a single channel having a constant inner diameter of about $\frac{1}{16}$ of an inch. The first tubing assembly 16a also includes a fitting 32a that allows the tubing 30 to be quickly connected to a first output port 26a of the first driver 14a. Similarly, the second tubing assembly 16b includes a fitting 32b that allows the tubing 30 to be quickly connected to a second output port 26b of the second driver 14b. In some arrangements, the fittings 32a and 32b are oversized tube barbs that provide high flow while holding the tubing 30 securely to the output ports 26a and 26b. At the other end of the tubing assemblies 16a and 16b, the tubing 30 fits over a first connector 34a and a second connector 34b coupled to the surgical cutter 12.

Figure 2:
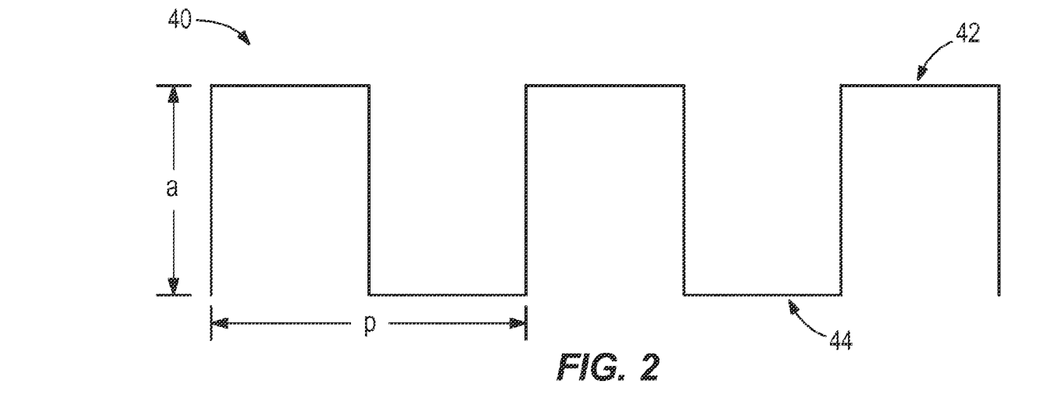
FIG. 2 is a graph of a desired waveform for pressure pulses used to operate the cutting apparatuses of FIGS. 1a and 1b.

The driver 14 (including the drivers 14a and 14b) generates pressure pulses in a predetermined waveform. For example, FIG. 2 illustrates an example waveform 40 of pressure pulses generated by the driver 14. The period (p) and amplitude (a) of the pressure pulses define the force and timing of the pressure pulses impacting the surgical cutter 12, which is translated into cutting actions by the surgical cutter 12. Ideally, the amplitude of each pressure pulse should have a high differential between its peak amplitude 42 (e.g., measured in pounds per square inch ("PSI") and its minimum amplitude 44 (e.g., also measured in PSI). This high differential creates a strong pressure pulse that provides sufficient and controlled force to the surgical cutter 12, which results in a precise cutting motion of the cutter. Precise cutting motion is particularly important when performing surgery within the small and delicate areas of an eye.

The waveform observed at the end of the tubing 30 coupled to the surgical cutter 12, however, normally contains many "defects" that make the waveform different than the relatively clean rectangular waveform generated by the driver 14. The defects may be partially caused by turbulence and high velocity of air flow at certain points or times in the tubing 30 or inside the driver 14. These defects impact the precision of the cutting performed by the surgical cutter 12. These defects become generally more extreme at higher cutting rates (e.g., when more than one pressure pulse is in the tubing 30 and traveling in different directions). This often occurs when pressure pulses having a frequency of about 45 Hz or more are transmitted in tubing having a length of approximately 80 inches (e.g., 78.7 inches).

To prevent or limit these waveform defects, the length of the tubing can be shortened. However, a longer length of tubing may be necessary based on the position of the driver 14 and the patient. For example, if tubing with a length substantially less than 80 inches is used to transmit pulse trains to the cutter 12, the driver 14 may be required to be located in close proximity to the patient or even on the patient, which may not be practical or desired. Alternatively, a vacuum can be applied to the inner channel of the tubing between pressure pulses. The vacuum creates a higher differential between a peak amplitude and minimum amplitude than when the tubing is vented to atmosphere. However, the use of the vacuum does not prevent any defects of the pressure pulses caused by turbulence or other high air velocity. In addition, the use of a vacuum increases the complexity and cost of the surgical equipment. Accordingly, these solutions have not adequately addressed the undesirable impact of these waveform defects on the performance of the cutter.

Figure 3A:
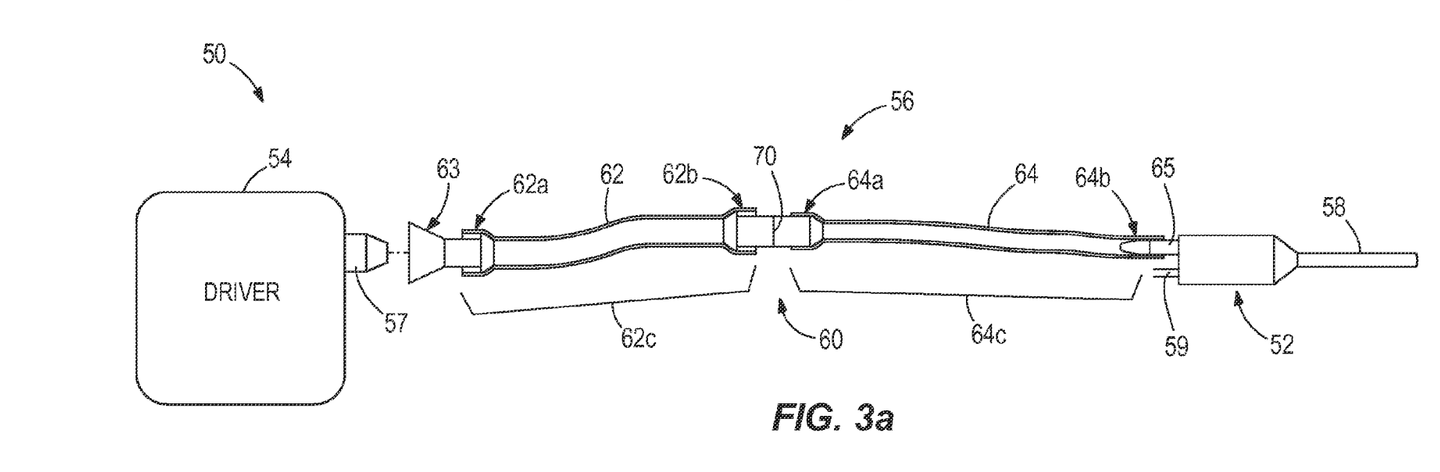
FIGS. 3a-3e schematically illustrate ophthalmic surgical cutting apparatuses according to embodiments of the present invention.

FIG. 3a schematically illustrates an ophthalmic surgical cutting apparatus 50 according to embodiments of the present invention. The apparatus 50 includes a surgical cutter 52, a pneumatic pulse generator or driver 54, and a tubing assembly 56. The surgical cutter 52 is similar to the surgical cutter 12 described above with respect to FIG. 1a. In particular, the surgical cutter 52 includes a hollow needle 58 and a cutter (not shown) contained inside the needle 58. In some arrangements, the surgical cutter 52 also includes an aspiration line 59 for connecting a vacuum to the cutter 52 to remove cut tissue.

The driver 54 is also similar to the driver 14 described above with respect to FIG. 1a. In particular, the driver 54 includes an output port 57 for transmitting pressure pulse trains to the surgical cutter 52. As described above for the driver 14, the driver 54 can generate pressure pulse trains at a fixed or a variable frequency, and, in some embodiments, a surgeon or other individual can control the driver 54 to generate pressure pulses at a desired frequency. The driver 54 can provide a similar range of frequencies as the driver 14 (e.g., about 2 Hz to about 83 Hz). In addition, in some embodiments, the driver 54 provides pressure pulses at higher frequencies. For example, the frequency could be about 133 Hz, about 167 Hz, or about 200 Hz.

The tubing assembly 56 connects the surgical cutter 52 to the driver 54. The tubing assembly 56 includes multi-stage tubing 60 that includes an inner channel that transmits the pressure pulses from the driver 54 to the cutter 52. The multi-stage tubing 60 has a total length of about two feet or more and, in some embodiments, has a length of about 80 inches (e.g., 78.7 inches).

Figure 6:
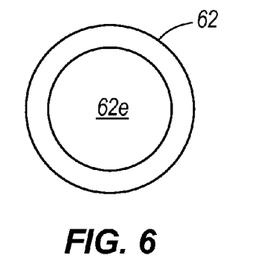
FIGS. 6 and 7 are cross-sectional views of the multi-stage tubing included in the cutting apparatuses of FIGS. 3a-3d.

Unlike the tubing 30 described above with respect to FIGS. 1a and 1b, the inner channel of the multi-stage tubing 60 has a non-constant cross-sectional area. In particular, as illustrated in FIG. 3, the multi-stage tubing 60 includes a first-stage tube 62 and a second-stage tube 64. The first-stage tube 62 has a first end 62a and a second end 62b opposite the first end 62a. The first end 62a is configured to be connected to the output port 57 of the driver 54 (e.g., through a fitting 63). The first-stage tube 62 has a first length 62c (see FIG. 4, not to scale) and a first inner channel 62d having a first cross-sectional area 62e (see FIG. 6, not to scale).

Figure 5:
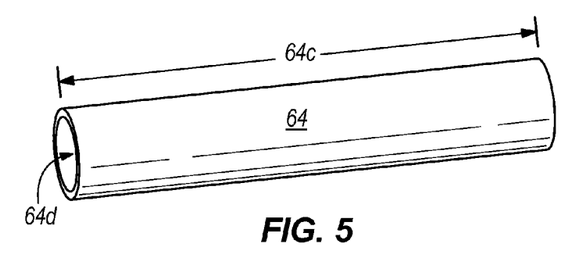
Figure 7:
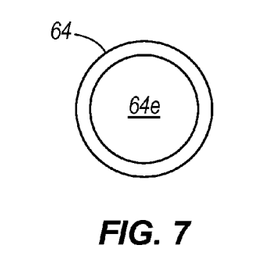

The second-stage tube 64 has a first end 64a and a second end 64b opposite the first end 64a. The first end 64a is configured to be connected to the second end 62b of the first-stage tube 62. In some embodiments, the second end 64b is configured to fit over a connector 65 coupled to the surgical cutter 12. The second-stage tube 64 has a second length 64c (see FIG. 5, not to scale) and a second inner channel 64d having a second cross-sectional area 64e (see FIG. 7, not to scale).

As illustrated in FIG. 3a, the first-stage tube 62 and the second-stage tube 64 are connected by one or more adapters 70, such as a double-barb fitting that fits within the inner channel of each tube 62 and 64. It should be understood that in other embodiments, the first-stage tube 62 and the second-stage tube 64 are formed as a single continuous piece of tubing. In these embodiments, the adapter 70 is not used. Nonetheless, distinct stages exist.

The second cross-sectional area 64e along a substantial portion of the second length 64c of the second-stage tube 64 is different than the first cross-sectional area 62e along a substantial portion of the length 64c of the first-stage tube 64 and, in some embodiments, is smaller than the first cross-sectional area 62e. For example, in some embodiments, the second inner channel 64d is cylinder-shaped and has a diameter of about 1/16 of an inch, and the first inner channel 62d is cylinder-shaped and has a diameter of about 3/32 of an inch. In some embodiments, the first cross-sectional area 62e and the second cross-sectional area 64e are each constant along the entire lengths 62d and 64d, respectively. However, in other embodiments, the cross-sectional area of one or both of the inner channels of the tubes 62 and 64 varies along the length of the tube. For example, the cross-sectional area of an inner channel may be varied to create a cone-shaped or wave-shaped channel for transmitting the pressure pulses. In these embodiments, the average cross-sectional area of the first inner channel 62d of the first-stage tube 62 is different than (e.g., larger than) the average cross-sectional area of the second inner channel 64d of the second-stage tube 64.

It should also be understood that although the cross-sectional areas of the first inner channel 62d and the second inner channel 64d are different, the first-stage tube 62 and the second-stage tube 62 may have different or the same overall (i.e., measured from their external surfaces) cross-sectional areas depending on the thickness of the walls of each tube defining the inner channel. Furthermore, although the first and second inner channels 62d and 64d are illustrated as having a cylinder-shape with a circular cross-sectional area, in some embodiments, at one or more points along the multi-stage tubing 60, the inner channel has a non-circular cross-sectional area. For example, the inner channel contained in the first-stage tube 62 and/or the second-stage tube 64 can have a polygonal-shaped (e.g., rectangular, hexagon, octagon, etc.) or a curved-shaped (e.g., oval) cross-sectional area. Also, in some embodiments, the tubes 62 and 64 each include one or more additional channels (e.g., a second pressure pulse channel may be used to return a cutter to a non-cutting position, instead of biasing the cutter as described above), and each additional channel may have the same or a different cross-sectional area than the areas 62e and 64e.

In some embodiments, the second length 64c of the second-stage tube 64 is also different than the first length 62c of the first-stage tube 62. For example, in one configuration the second length 64c is less than the first length 62c of the first-stage tube 62 (see FIG. 3e). In some embodiments, the ratio of the first length 62c to the second length 64c is about 6 to 1.

Figure 8:
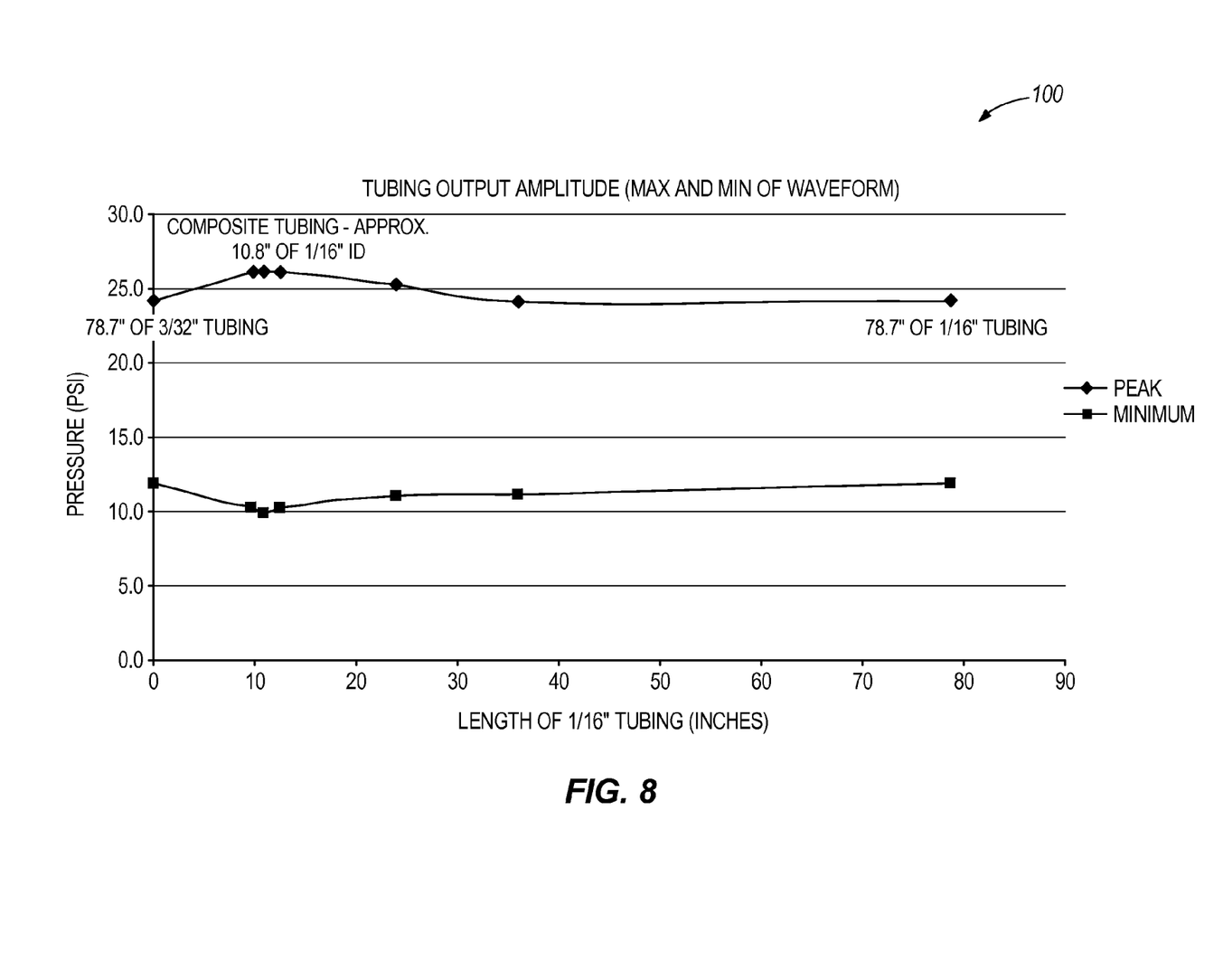
FIG. 8 is a graph illustrating pressure pulse amplitudes for various multi-stage tubing configurations.

FIG. 8 is a graph 100 illustrating the peak and minimum amplitude of pressure pulses transmitted along various configurations of the multi-stage tubing 60 having an overall fixed length of about 80 inches (e.g., 78.7 inches) and having various second lengths 64c of the second-stage tube 64 (e.g., using a 133 Hz drive frequency). The measured amplitudes are the amplitudes measured at the end of the tubing assembly normally coupled to the surgical cutter. Therefore, the measured amplitudes represent the peak and minimum of the pulses received at the surgical cutter. As described above, to provide proper cutting motion, the differential between the peak and minimum amplitude of the pressure pulse should be as large as possible.

As illustrated in FIG. 8, when the prior art continuous tubing 30 (having an inner cylinder-shaped channel with a constant diameter) is used to transmit pressure pulses, the peak amplitude of the pulses is about 24.5 PSI and the minimum amplitude of the pulses is about 11.9 PSI. However, as shown in FIG. 8, when the multi-stage tubing 60 is used to transmit pressure pulses (with stages having inner channels with different cross-sectional areas), the peak and minimum of the pressure pulses are at least the same as those for the continuous tubing 30 and, in many configurations, are better. In particular, the pressure pulse reaches a peak amplitude of about 26.2 PSI and a minimum amplitude of 10.3 PSI when the multi-stage tubing 60 is used with a second-stage tube 64 that has a second length 64c of about 11 inches (and, consequently, a first-stage tube 62 having a first length 62c of about 68 inches when the multi-stage tubing 60 has a total or combined length of about 80 inches). Other lengths of the first-stage tube 62 and the second-stage tube 64 can also be used that result in better peak and minimum amplitudes than when the continuous tubing 30 is used. For example, TABLE 1 below provides the peak and minimum (or "residual") amplitudes of the pressure pulses using various lengths of the second-stage tube 64 (and, subsequently, various lengths of the first-stage tube 62 assuming the tubing 60 has a combined length of about 78.7 inches).

TABLE 1

| Second-Stage Tube Length (in inches) | Peak PSI | Residual PSI | Average PSI | First Harmonic dBm |
| --- | --- | --- | --- | --- |
| 0.0 | 24.2 | 11.9 | 18.8 | −14.74 |
| 9.8 | 26.2 | 10.2 | 18.9 | −12.47 |
| 10.8 | 26.2 | 9.7 | 18.6 | −12.12 |
| 12.5 | 26.2 | 10.3 | 18.8 | −12.35 |
| 24 | 25.3 | 11.1 | 18.7 | −13.59 |
| 36 | 24.1 | 11.2 | 18.7 | −14.8 |
| 78.7 | 24.2 | 11.9 | 18.9 | −15.31 |

Therefore, as shown in FIG. 8 and TABLE 1, using the multi-stage tubing 60 generally results in the surgical cutter receiving an improved pressure pulse as compared to when the continuous tubing 30 is used. In particular, the inventors believe that propagating the pressure pulse through a higher-volume but lower-loss tube, such as the first-stage tube, and then through a lower-volume but higher-loss tube, such as the second-stage tube, results in an improved pressure pulse received by the surgical cutter.

Figure 9:
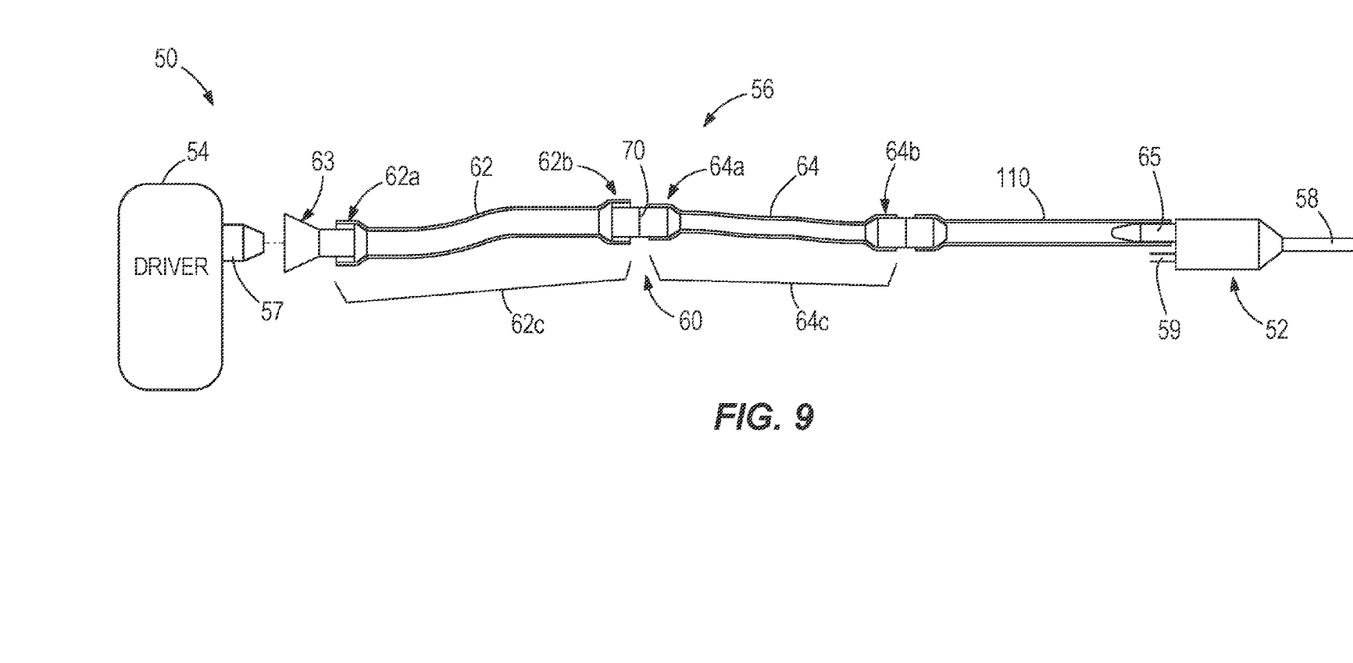
FIG. 9 schematically illustrates an ophthalmic surgical cutting apparatus with three-stage tubing according to an embodiment of the present invention.

It should be understood that the multi-stage tubing 60 can include additional tubes. For example, as illustrated in FIG. 9, in some embodiments, the multi-stage tubing 60 includes a third-stage tube 110. The third-stage tube 110 has a first end, a second end opposite the first end, and an inner channel. The first end of the third-stage tube 110 is in pneumatic communication with the second end 64b of the second-stage tube 64 and the second end of the third-stage tube 110 is in pneumatic communication with the surgical cutter 52. In some embodiments, the inner channel of the third-stage tube 110 has the same cross-sectional area as the first-stage tube 62. In this configuration, the tubing assembly 56 provides three-stage tubing that includes a middle stage (i.e., the second-stage tube 64) that has a smaller diameter (or cross-sectional area) than the two end stages (i.e., the first-stage tube 62 and the third-stage tube 110). It should be understood, however, that the inner channel of the third-stage tube 110 (and any other tubes included in the multi-stage tubing 60) can have a different cross-sectional area than the first-stage tube 62 and can have the same or a different cross-sectional area than the second-stage tube. For example, when the tubing assembly 56 provides three-stage tubing, the three-stage tubing can include an inner channel that has a middle stage (i.e., the second-stage tube 64) that has a larger cross-sectional area than the two end stages (i.e., the first-stage tube 62 and the third-stage tube 110). Also, in some embodiments, each inner channel of the three tubes may have a different cross-sectional area and may create a channel that decreases in cross-sectional area as it reaches the surgical cutter. For example, in some arrangements, the first-stage tube 62 has an inner channel 62d that has a first diameter (e.g., about 4/32 of an inch), the second-stage tube 64 has an inner channel 64d that has a second diameter smaller than the first diameter (e.g., about 3/32 of an inch), and the inner channel of the third-stage tube 110 has a third diameter smaller than the second diameter (e.g., about 1/16 of an inch). If additional tubes are included in the multi-stage tubing 60, the tubes may form similar patterns as described above for the three-stage tubing.

Figure 3B:
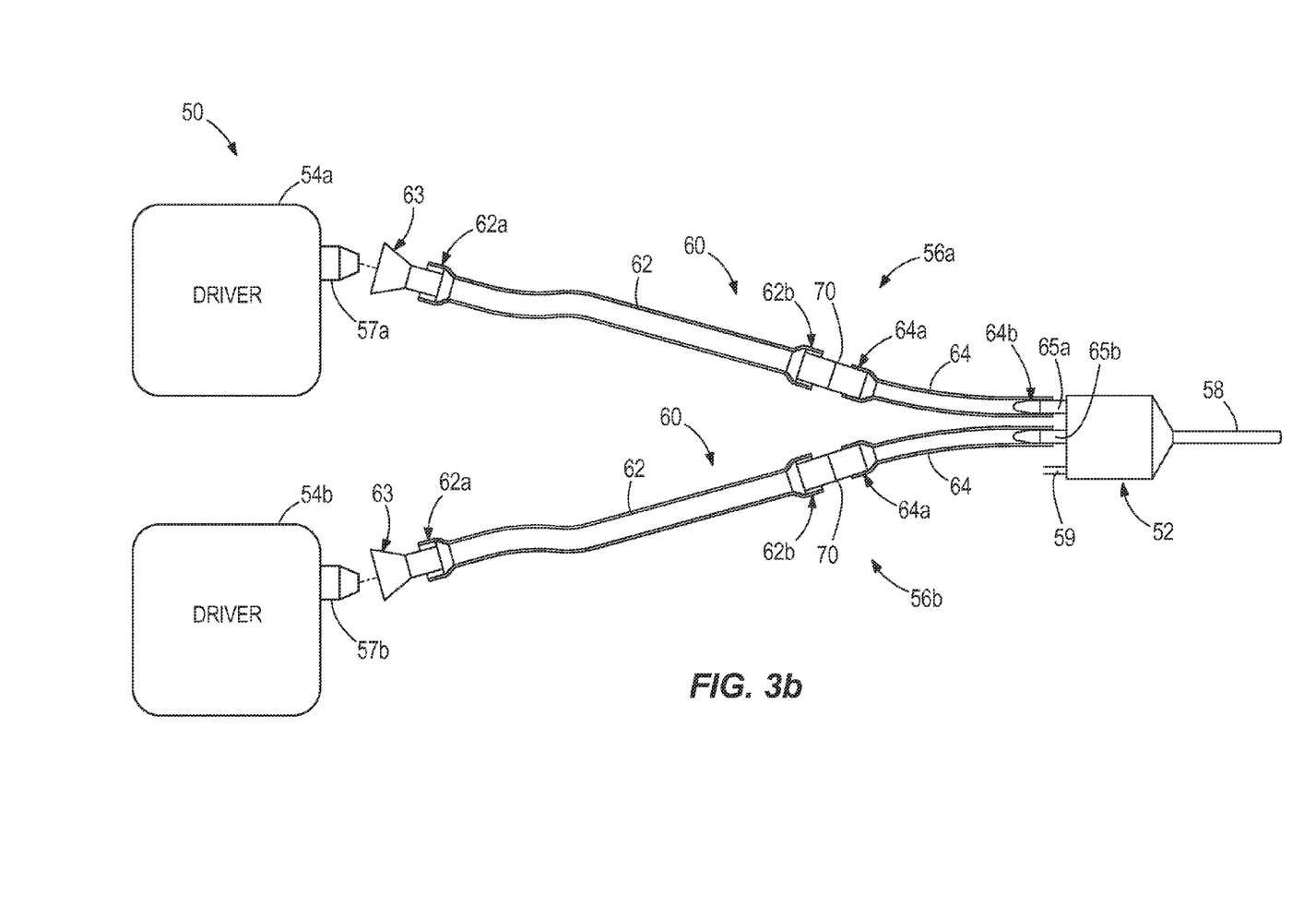

It should be understood that the multi-stage tubing 60 can be used in embodiments where two pressure pulses or pulse trains are used to drive the cutter. For example, as illustrated in FIG. 3b, in one alternative, two tubing assemblies are used to convey pressure pulses to the surgical cutter 12 and one or both of the tubing assemblies can include the multi-stage tubing 60 as described above. In particular, as illustrated in FIG. 3b, a first driver 54a transmits pressure pulses to the surgical cutter 52 via a first tubing assembly 56a to force the cutter into the cutting position. A second driver 54b transmits pressure pulses to the cutter via a second tubing assembly 56b to restore the cutter to the non-cutting position. In some embodiments, the two drivers 54a and 54b are embodied as a single device. The single device can include two pulse generators, each with a separate output (see FIG. 3c). In other embodiments, the single device can include a single pulse generator that supplies pressure pulses or pulse trains over two different outputs at different amplitudes, frequencies, and/or phases (see FIG. 3d).

As illustrated in FIG. 3b, one or both of the first and second tubing assemblies 56a and 56b have similar properties as the tubing assembly 56 described above with respect to FIG. 3a. In particular, one or both of the tubing assemblies 56a and 56b includes the multi-stage tubing 60 described above with respect to FIG. 3a. Therefore, one or both of the tubing assemblies 56a and 56b includes the first-stage tube 62 and the second-stage tube 64 as described above with respect to FIG. 3a.

In particular, in some embodiments, the first tubing assembly 56a includes the first-stage tube 62 and the second-stage 64. The first-stage tube 62 has a first end 62a and a second end 62b opposite the first end 62a. The first end 62a is configured to be connected to a first output port 57a of the first driver 54a (e.g., through a fitting 63). The second-stage tube 64 has a first end 64a and a second end 64b opposite the first end 64a. The first end 64a is configured to be connected to the second end 62b of the first-stage tube 62. In some embodiments, the second end 64b is configured to fit over a connector 65a coupled to the surgical cutter 12. The first-stage tube 62 and second-stage tube 64 can be connected by an adapter 70 or can be formed as a single continuous piece of tubing.

Similarly, in some embodiments, the second tubing assembly 56b includes the first-stage tube 62 and the second-stage 64. The first-stage tube 62 has a first end 62a and a second end 62b opposite the first end 62a. The first end 62a is configured to be connected to a second output port 57b of the second driver 54b (e.g., through a fitting 63). The second-stage tube 64 has a first end 64a and a second end 64b opposite the first end 64a. The first end 64a is configured to be connected to the second end 62b of the first-stage tube 62. In some embodiments, the second end 64b is configured to fit over a connector 65b coupled to the surgical cutter 12. The first-stage tube 62 and second-stage tube 64 can be connected by an adapter 70 or can be formed as a single continuous piece of tubing.

Figure 3C:
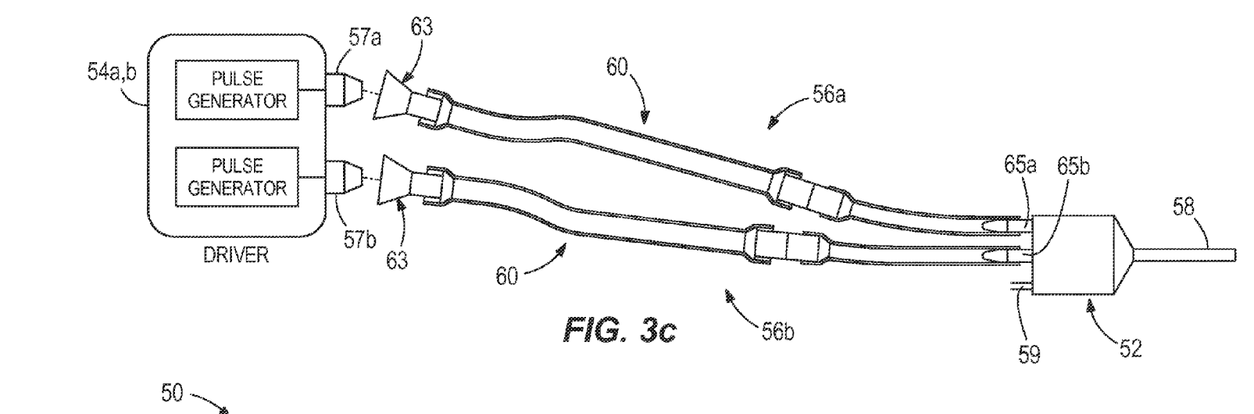
Figure 3D:
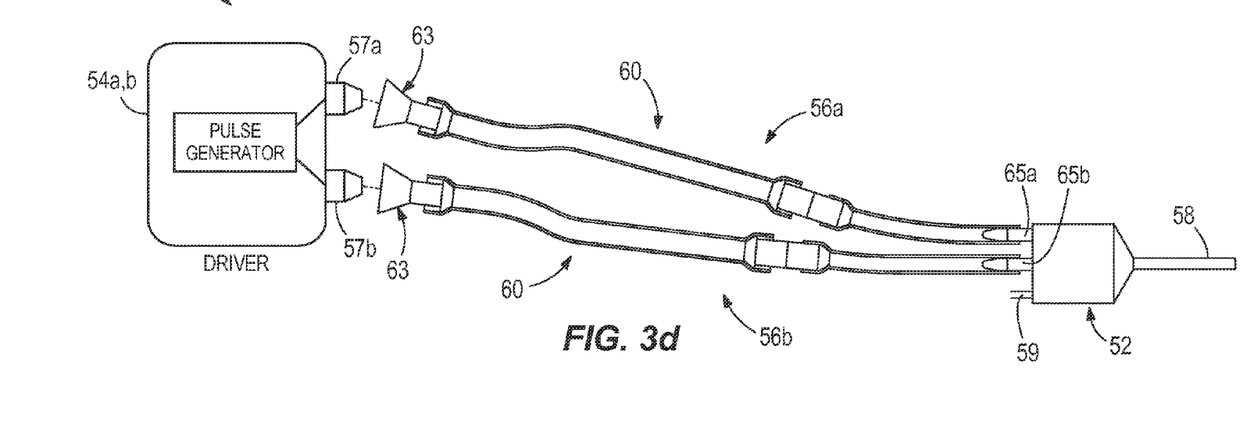
Figure 3E:
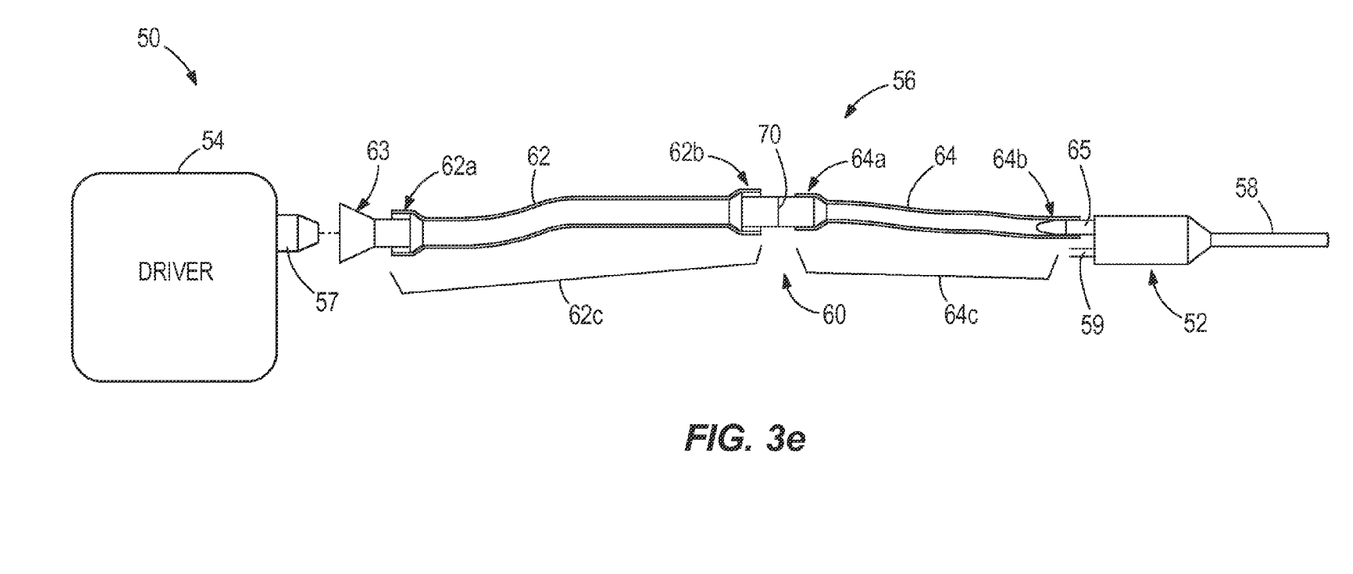
Figure 4:
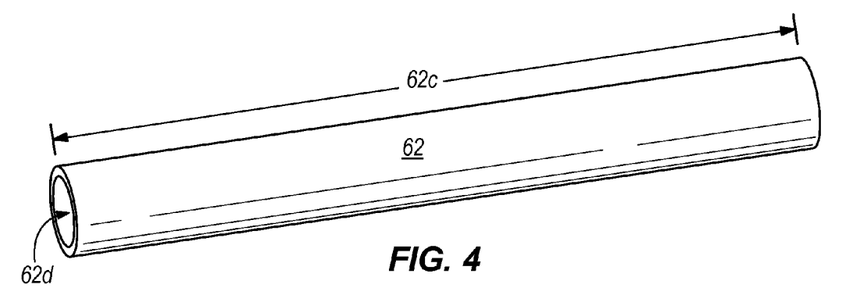
FIGS. 4 and 5 are perspective views of the multi-stage tubing included in the cutting apparatuses of FIG. 3a-3d.

It should be understood that in the embodiments of FIGS. 3b-3d, one or both of the tubing assemblies 56a and 56b can include the multi-stage tubing 60. For example, in some embodiments, only one of the first and second tubing assemblies 56a and 56b include the multi-stage tubing 60 and the other tubing assembly includes the prior art tubing 30 described above with respect to FIG. 1b. Furthermore, in some embodiments, more than two tubing assemblies 56 are connected to the surgical cutter 56 and, in these embodiments, at least one of the tubing assemblies includes the multi-stage tubing 60 as described above. In addition, it should be understood that the tubing assemblies 56a and 56b can include all of the various configurations of the multi-stage tubing 60 as described above with respect to FIG. 3a.

It should be understood that (and as is indicated above) the term "multi-stage" as used in the present application is not limited to tubing including individual pieces of tubing each having an inner channel having a constant cross-sectional area along the entire length of the individual piece of tubing. In particular, the term "multi-stage" also encompasses a single, continuous piece of tubing that includes an inner channel that has at least two different cross-sectional areas at various points along the length of the tubing (i.e., at least two stages). In addition, when the multi-stage tubing includes individual pieces of tubing or a single, continuous piece of tubing, the tubing may an inner channel having two or more different cross-sectional areas that are constructed in a step-wise fashion (e.g., 1/16 of an inch stepped to 3/32 of an inch) or in a continuously-variable fashion (e.g., 1/16 of an inch continuously increased over a length of tubing to 3/32 of an inch). When different cross-sectional areas or inner diameters are constructed in a continuously-variable fashion, the multi-stage tubing may include an infinite number of "stages," wherein at least two of the "stages" have an inner channel with different cross-sectional areas. Various combinations of these multi-stage tubing configurations are also possible. For example, the multi-stage tubing can include a continuous piece of tubing that includes an inner channel with two or more different cross-sectional areas constructed in a step-wise fashion and two or more different cross-sectional areas constructed in a continuously-variable fashion. The multi-stage tubing can also include a continuous piece of tubing with an inner channel including at least two different cross-sectional areas (e.g., representing a first and second "stage" of tubing) and an individual piece of tubing coupled (e.g., through use of an adaptor) to the continuous piece of tubing (e.g., representing a third "stage" of tubing) or vice versa.

Various features of the invention are set forth in the following claims.

What is claimed is:

1. An ophthalmic surgical cutting apparatus, the apparatus comprising:
   a pneumatically-powered surgical cutter; and
   a pneumatic tubing assembly comprising multi-stage tubing transmitting pneumatic pressure pulses from a pneumatic pulse generator to the pneumatically-powered surgical cutter, the multi-stage tubing including
   a first-stage, the first-stage having
      a first end coupled to an output port of the pneumatic pulse generator through a fitting attached to the first end,
      a second end opposite the first end, and
      a first inner channel for transmitting the pressure pulses to the pneumatically-powered surgical cutter, the first inner channel having a first cross-sectional area, and
   a second-stage, the second-stage having
      a first end in pneumatic communication with the second end of the first-stage,
      a second end opposite the first end of the second-stage coupled to the pneumatically-powered surgical cutter, and
      a second inner channel for transmitting the pneumatic pressure pulses to the pneumatically-powered surgical cutter, the second inner channel having a second cross-sectional area different than the first cross-sectional area.

2. The cutting apparatus of claim 1, wherein the second cross-sectional area is smaller than the first cross-sectional area.

3. The cutting apparatus of claim 1, wherein the first-stage has a first length and the second-stage has a second length.

4. The cutting apparatus of claim 3, wherein the second length is shorter than the first length.

5. The cutting apparatus of claim 3, wherein the second length is about 11 inches.

6. The cutting apparatus of claim 3, wherein the first cross-sectional area is substantially constant along the entire first length.

7. The cutting apparatus of claim 3, wherein the second cross-sectional area is substantially constant along the entire second length.

8. The cutting apparatus of claim 3, wherein a ratio of the first length to the second length is about 6 to 1.

9. The cutting apparatus of claim 1, wherein the tubing assembly includes an adapter coupling the first-stage to the second-stage.

10. The cutting apparatus of claim 9, wherein the adapter fits within the first inner channel of the first-stage and the second inner channel of the second-stage.

11. The cutting apparatus of claim 1, wherein the multi-stage tubing comprises a continuous single piece of tubing including the first-stage and the second-stage.

12. The cutting apparatus of claim 11, wherein the continuous single piece of tubing includes the first-stage and the second-stage constructed in a step-wise fashion.

13. The cutting apparatus of claim 11, wherein the continuous single piece of tubing includes the first-stage and the second-stage constructed in a continuously-variable fashion.

14. The cutting apparatus of claim 11, wherein the continuous single piece of tubing includes an inner channel having a continuously-variable cross-sectional area over substantially an entire length of the continuous single piece of tubing.

15. The cutting apparatus of claim 1, wherein the multi-stage tubing includes a third-stage having
a first end in pneumatic communication with the second end of the first-stage,
a second end opposite the first end of the third-stage in pneumatic communication with the first end of the second-stage, and
a third inner channel for transmitting the pressure pulses to the surgical cutter, the third inner channel having a third cross-sectional area.

16. The cutting apparatus of claim 15, wherein the third cross-sectional area is different than at least one of the first cross-sectional area and the second cross-sectional area.

17. The cutting apparatus of claim 15, wherein the third cross-sectional area is larger than at least one of the first cross-sectional area and the second cross-sectional area.

18. The cutting apparatus of claim 15, wherein the third cross-sectional area is smaller than at least one of the first inner transverse dimension and the second inner transverse dimension.

19. The cutting apparatus of claim 1, wherein the first cross-sectional area is a circular cross-sectional area with a diameter of about 3/32 of an inch and the second cross-sectional area is a circular cross-sectional area with a diameter of about 1/16 of an inch.

20. The cutting apparatus of claim 1, wherein the pneumatic tubing assembly transmits the pneumatic pressure pulses to the pneumatically-powered surgical cutter at a rate of approximately 40 Hz.

21. The cutting apparatus of claim 1, wherein the pneumatic tubing assembly transmits the pneumatic pressure pulses to the pneumatically-powered surgical cutter at a rate of approximately 80 Hz.

22. The cutting apparatus of claim 1, wherein at least one of the first cross-sectional area and the second cross-sectional area is a non-circular cross-sectional area.

23. The ophthalmic surgical cutting apparatus of claim 1, wherein the first cross-sectional area of the first inner channel is circular.

24. The ophthalmic surgical cutting apparatus of claim 1, wherein the second cross-sectional area of the second inner channel is circular.

25. A pneumatic cutting system comprising:
a pneumatic pulse generator;
a pneumatically-powered surgical cutter; and
multi-stage tubing transmitting pneumatic pressure pulses from the pneumatic pulse generator to the pneumatically-powered surgical cutter, the multi-stage tubing including
a first-stage, the first-stage having
a first end coupled to an output port of the pneumatic pulse generator through a fitting attached to the first end,
a second end opposite the first end, and
a first inner channel for transmitting the pneumatic pressure pulses to the pneumatically-powered surgical cutter, the first inner channel having a first cross-sectional area, and
a second-stage, the second-stage having
a first end in pneumatic communication with the second end of the first-stage,
a second end opposite the first end of the second-stage coupled to the pneumatically-powered surgical cutter, and
a second inner channel for transmitting the pneumatic pressure pulses to the pneumatically-powered surgical cutter, the second inner channel having a second cross-sectional area different than the first cross-sectional area.

26. The tubing assembly of claim 25, wherein the second cross-sectional area is smaller than the first cross-sectional area.

27. The tubing assembly of claim 25, wherein the first-stage has a first length and the second-stage has a second length.

28. The tubing assembly of claim 27, wherein the second length is shorter than the first length.

29. The tubing assembly of claim 27, wherein the second length is about 11 inches.

30. The tubing assembly of claim 27, wherein the first cross-sectional area is substantially constant along the entire first length.

31. The tubing assembly of claim 27, wherein the second cross-sectional area is substantially constant along the entire second length.

32. The tubing assembly of claim 27, wherein a ratio of the first length to the second length is about 6 to 1.

33. The tubing assembly of claim 25, further comprising an adapter coupling the first-stage to the second-stage.

34. The tubing assembly of claim 33, wherein the adapter fits within the first inner channel of the first-stage and the second inner channel of the second-stage.

35. The tubing assembly of claim 25, wherein the multi-stage tubing comprises a continuous single piece of tubing including the first-stage and the second-stage.

36. The tubing assembly of claim 35, wherein the continuous single piece of tubing includes the first-stage and the second-stage constructed in a step-wise fashion.

37. The tubing assembly of claim 35, wherein the continuous single piece of tubing includes the first-stage and the second-stage constructed in a continuously-variable fashion.

38. The tubing assembly of claim 35, wherein the continuous single piece of tubing includes an inner channel having a continuously-variable cross-sectional area over substantially an entire length of the continuous single piece of tubing.

39. The tubing assembly of claim 25, wherein the multi-stage tubing includes a third-stage having
- a first end in pneumatic communication with the second end of the first-stage,
- a second end opposite the first end of the third-stage in pneumatic communication with the first end of the second-stage, and
- a third inner channel for transmitting the pressure pulses to the surgical cutter, the third inner channel having a third cross-sectional area.

40. The tubing assembly of claim 39, wherein the third cross-sectional area is different than at least one of the first cross-sectional area and the second cross-sectional area.

41. The tubing assembly of claim 39, wherein the third cross-sectional area is larger than at least one of the first cross-sectional area and the second cross-sectional area.

42. The tubing assembly of claim 39, wherein the third cross-sectional area is smaller than at least one of the first cross-sectional area and the second cross-sectional area.

43. The tubing assembly of claim 25, wherein the first cross-sectional area is a circular cross-sectional area with a diameter of about 3/32 of an inch and the second cross-sectional area is a circular cross-sectional area with a diameter of about 1/16 of an inch.

44. The tubing assembly of claim 25, wherein the multi-stage tubing transmits the pneumatic pressure pulses to the pneumatically-powered surgical cutter at a rate of approximately 40 Hz.

45. The tubing assembly of claim 25, wherein the multi-stage tubing transmits the pneumatic pressure pulses to the pneumatically-powered surgical cutter at a rate of approximately 80 Hz.

46. The tubing assembly of claim 25, wherein at least one of the first cross-sectional area and the second cross-sectional area is a non-circular cross-sectional area.

47. An ophthalmic surgical cutting apparatus, the apparatus comprising:
- a pneumatically-powered surgical cutter; and
- multi-stage tubing transmitting pneumatic pressure pulses to the pneumatically-powered surgical cutter from a pneumatic pulse generator, the multi-stage tubing including
- a first-stage, the first-stage having
  - a first end to be coupled to an output port of the pneumatic pulse generator through a fitting attached to the first end,
  - a second end opposite the first end, and
  - a first inner channel for transmitting the pressure pulses to the pneumatically-powered surgical cutter, the first inner channel having a first cross-sectional area, and
- a second-stage, the second-stage having
  - a first end in pneumatic communication with the second end of the first-stage,
  - a second end opposite the first end of the second-stage coupled to the pneumatically-powered surgical cutter, and
  - a second inner channel for transmitting the pneumatic pressure pulses to the pneumatically-powered surgical cutter, the second inner channel having a second cross-sectional area different than the first cross-sectional area.

* * * * *